United States Patent
Klauke et al.

Patent Number: 5,565,614
Date of Patent: Oct. 15, 1996

[54] 2,4,5-TRIHALOGENO-AND 2,3,4,5-TETRAHALOGENOBENZENE DERIVATIVES

[75] Inventors: Erich Klauke, Odenthal; Uwe Petersen, Leverkusen; Klaus Grohe, Odenthal, all of Germany

[73] Assignee: Bayer Aktiengesellschaft, Leverkusen, Germany

[21] Appl. No.: 419,969

[22] Filed: Apr. 7, 1995

Related U.S. Application Data

[60] Continuation of Ser. No. 284,331, Aug. 2, 1994, which is a division of Ser. No. 968,603, Oct. 29, 1992, Pat. No. 5,362,909, which is a division of Ser. No. 763,027, Sep. 20, 1991, Pat. No. 5,200,548, which is a division of Ser. No. 459,876, Jan. 2, 1990, Pat. No. 5,072,038, which is a continuation of Ser. No. 735,502, May 17, 1985, abandoned.

[30] Foreign Application Priority Data

Jun. 4, 1984 [DE] Germany .......................... 34 20 796.1

[51] Int. Cl.$^6$ .................................................. C07C 51/58
[52] U.S. Cl. ............................................................. 562/849
[58] Field of Search ............................................... 562/849

[56] References Cited

U.S. PATENT DOCUMENTS

| | | |
|---|---|---|
| 3,230,268 | 1/1966 | Kobayashi et al. . |
| 3,485,865 | 12/1969 | Richter et al. . |
| 4,439,620 | 3/1984 | Klauke et al. . |
| 4,549,994 | 10/1985 | Hagemann et al. . |
| 4,556,658 | 12/1985 | Grohe et al. . |
| 4,582,948 | 4/1986 | Tank et al. . |
| 4,791,225 | 12/1988 | Irikura et al. . |
| 4,792,618 | 12/1988 | Bieron et al. . |

FOREIGN PATENT DOCUMENTS

| | | |
|---|---|---|
| 0057844 | 8/1982 | European Pat. Off. . |
| 2503269 | 8/1979 | Germany . |
| 0028493 | 11/1969 | Japan . |
| 8035161 | 3/1983 | Japan . |
| 9184149 | 10/1984 | Japan . |
| 0023358 | 2/1985 | Japan . |
| 0036453 | 2/1985 | Japan . |
| 0977963 | 12/1964 | United Kingdom . |
| 2142018 | 1/1985 | United Kingdom . |
| 0007267 | 12/1987 | WIPO . |

OTHER PUBLICATIONS

Birchall, J. Metal, J. Chem. Soc. (C) (7) 1341–2, 1971.
Organicum, 3 Aufl. (1964), p. 438.
J. I. DeGraw et al., J. Cehm. Eng., vol. 13, 587–8 (1968).
J. Med. Chem 26, 1116–1122 (1983).
Japanese Laid Open (Kokai) Patent Publication No. 150543 (1983) Abstract.
Japanese Laid Open (Kokai) Patent Publication No. 233089 (1985) (Abstract).
Japanese Laid Open (Kokai) Patent Publication No. 72885 (1985) (Abstract).
Yokobson et al, Chemical Abstracts, vol. 64, Colms. 14124–5 (1966).
Chisso, Chemical Abstracts, vol. 100, #51279p (1984).

*Primary Examiner*—Paul J. Killos
*Attorney, Agent, or Firm*—Sprung Horn Kramer & Woods

[57] ABSTRACT

2,4,5-Trihalogenobenzene derivatives of the formula

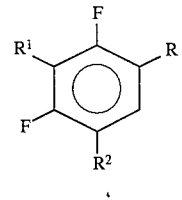

is which
R is —COOH, —COCl, —COF, —CN, —CONH$_2$, —CH$_2$OH, —CH$_2$Cl, —CHCl$_2$, —CCl$_3$ or —CHO,
R$^1$ is H, Cl or F, and
R$^2$ is Cl or F,
it only being possible for R$^1$ or R$^2$ to be F, and processes for their preparation starting from benzonitriles reacted with potassium fluoride. The novel compounds are intermediates for antibacterials such as quinolone carboxylic acids.

3 Claims, No Drawings

2,4,5-TRIHALOGENO-AND 2,3,4,5-TETRAHALOGENOBENZENE DERIVATIVES

This application is a continuation of application Ser. No. 08/284,331, filed Aug. 2, 1994, now allowed, which is a division of Ser. No. 07/968,603 filed Oct. 29, 1992 now U.S. Pat. No. 5,362,909; which is a division of Ser. No. 07/763,027 filed Sep. 20, 1991 now U.S. Pat. No. 5,200,548; which is a division of Ser. No. 07/459,876 filed Jan. 2, 1990 now U.S. Pat. No. 5,072,038; which is a continuation of Ser. No. 06/735,502 filed May 17, 1985, now abandoned.

The present invention relates to 2,4,5-trihalogeno- and 2,3,4,5-tetrahalogenobenzene derivatives and process for their preparation. The compounds according to the invention are valuable intermediates for the synthesis of highly active antibacterial medicaments.

2,4,5-Trihalogeno- and 2,3,4,5-tetrahalogenobenzene derivatives of the formula (I)

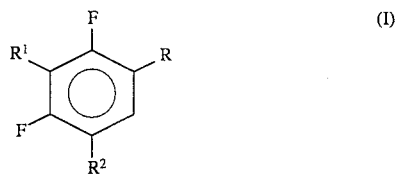

in which

R represents —COOH, —COCl, —COF, —CN, —CONH$_2$, —CH$_2$OH, —CH$_2$Cl, —CHCl$_2$, —CCl$_3$ or —CHO, R$^1$ represents H, Cl or F and R$^2$ represents Cl or F, it only being possible for R$^1$ or R$^2$ to be F, have been found.

The following may be particularly mentioned:
2,4,5-trifluorobenzoyl fluoride;
2,3,4-trifluoro-5-chlorobenzoyl fluoride;
2,4,5-trifluoro-3-chlorobenzoyl chloride;
2,4-difluoro-3,5-dichlorobenzoyl fluoride.

It has also been found that the 2,4,5-trihalogeno- and 2,3,4,5-tetrahalogenobenzene derivatives of the formula (I)

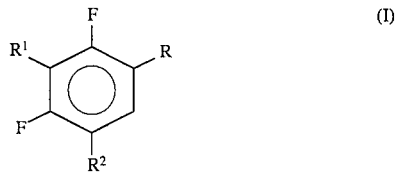

in which

R represents —COOH, —COCl, —COF, —CN, —CONH$_2$, —CH$_2$OH, —CH$_2$Cl, —CHCl$_2$, —CCl$_3$ or —CHO, R$^1$ represents H, Cl or F and R$^2$ represents Cl or F, it only being possible for R$^1$ or R$^2$ to be F, are obtained by reacting 2,3,4,5-tetrachlorobenzonitrile with potassium fluoride in a solvent at elevated temperature, and converting the resulting nitriles into the compounds of the formula (I) in a manner known per se.

It has also been found that 2,3,4,5-tetrahalogenobenzene derivatives of the formula (II)

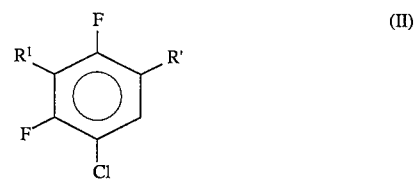

in which

R' represents —COCl or —COF, and

R$^1$ represents Cl or F, can be obtained by reacting 2,3,4,5-tetrachlorobenzoyl chloride or 2,3,4,5-tetrachlorobenzoyl fluoride (see European Patent No. 57,844), where appropriate after fluorination with hydrofluoric acid, with potassium fluoride in a solvent at elevated temperature.

The quantity of potassium fluoride to be used depends on the number of chlorine atoms which are to be exchanged. At least one mole of KF is used, but in general 1.1–1.5 mole, for 1 chlorine atom. A maximum of 2 moles of KF is used for 1 chlorine; beyond this, the quantity of KF has virtually no effect on the degree of fluorination, and the process becomes uneconomic. However, it is possible to save part of the costly KF when the 2,3,4,5-tetrachlorobenzoyl chloride is previously fluorinated with hydrofluoric acid, and the 2,3,4,5-tetrachlorobenzoyl fluoride, which results in virtually quantitative yield from this reaction, is used for the Cl/F exchange reaction with KF. Because of the greater activation by the more electronegative fluorocarbonyl group, its greater thermal stability, and the reduced load of KCl in the reaction mixture, this two-stage fluorination leads to an overall improvement in the balance of the nuclear fluorination.

The solvents which can be used for the nuclear fluorination are the inert solvents known for fluorination reactions, for example dimethylformamide, dimethyl sulphoxide, N-methylpyrrolidone, diethyl sulphone etc. However, tetramethylene sulphone (sulpholane) is particularly preferably used.

The reaction temperature is between 160° and 260° C., depending on the desired degree of fluorination. While product containing no fluorine in the nucleus is still found at the lower temperature, a very evident proportion of the known 2,3,4,5-tetrafluorobenzoyl fluoride is already produced at the higher temperatures (see German Patent Application P 33 18 145, corresponding to U.S. application Ser. No. 603,480 filed Apr. 24, 1984, now pending).

Because of the thermal instability of the tetrahalogenobenzoyl halides present in the reaction mixture—preferential formation of octahalogenobenzophenones—it has proved to be advantageous to remove the desired reaction product continuously from the reaction space by distillation during the fluorination reaction. This is advantageously carried out via a fractionating column, continuously adjusting the distillation pressure to the partial pressure of the fluorination mixture.

It has also been found that 2,4,5-trifluoro-3-chlorobenzoyl chloride can be obtained by reacting 2,4,5-trifluorobenzoyl chloride to give 2,4,5-trifluoro-3-chlorobenzoic acid and reacting the latter with thionyl chloride. The 2,4,5-trifluorobenzoic acid required as starting material for this has already been disclosed [J. I. de Graw, M. Cory, W. A. Skinner, J. Chem. Eng. Data 13, 587 (1968)]. Its preparation according to this literature citation is carried out, in very poor yield, from 2-amino-4,5-difluorobenzoic esters by NH$_2$/F exchange in the manner of a Balz-Schiemann reaction. However, 2,4 -dichloro-5-fluorobenzoyl chloride has been disclosed in DE-OS (German Published Specification) 3,142,856=U.S. Pat. No. 4,439,620. It has now also been found that from this, by fluorination with KF in a solvent, preferably tetramethylene sulphone, at temperatures from 180° to 230° C., the new 2,4,5-trifluorobenzoyl fluoride is obtained in a straightforward manner and in good yield, and the latter is converted virtually quantitatively into 2,4,5-trifluorobenzoic acid by alkaline hydrolysis.

the chlorination of the 2,4,5-trifluorobenzoic acid is carried out in the melt, under pressure and/or in a solvent, for example chlorosulphonic acid or oleum, in the presence of halogen transfer agents, for example iodine. 2,4,5-Trifluoro-3-chlorobenzoic acid is obtained in this reaction. However, since the reaction mixture still contains unchanged starting material and some 2,4,5-trifluoro-3,6-dichlorobenzoic acid, the crude mixture is treated, without intermediate isolation, with thionyl chloride. The desired 2,4,5-rifluoro-3-chlorobenzoyl chloride is then obtained by fractional distillation. However, it is more favorable to carry out the separation by distillation of the acid fluorides.

the functionalization of the nitriles to give the corresponding acid halides is carried out by, for example, hydrolysis to the carbonxylic acid and conversion into acid chlorides using thionyl chloride. The acid fluorides are then obtained from the acid chlorides by reaction with fluorinating agents, for example anhydrous hydrofluoric acid or alkali metal fluorides. Conversely, if it is desired to prepare the acid chloride from an acid fluoride, then this is carried out by reaction with SiCl$_4$, where appropriate in the presence of catalytic quantities of aluminum chloride. Halogen-substituted benzyl alcohols can be prepared in a smooth reaction from the acid halides, especially well from the acid fluorides, by reduction with sodium borohydride.

From the halogenated benzyl alcohols, using thionyl chloride the corresponding benzyl chlorides are obtained in virtually quantitative yield, and the latter can undergo further stepwise chlorination with gaseous chlorine to give the corresponding benzal chlorides and benzotrichlorides.

The halogenated benzaldehydes are obtained by, preferably acid, hydrolysis of the halogenated benzal chlorides, while corresponding hydrolysis of the halogenated benzotrichlorides provides both the corresponding acid chlorides and the acids.

The compounds according to the invention are intended for use as starting materials for the synthesis of medicaments.

The compounds according to the invention can be converted, for example, into highly active antibacterial 1-cyclopropyl-6,8-dihalogeno-1,4-dihydro-4-oxo-7-(1-piperazinyl)-3-quinolinecarboxylic acids. The synthesis can be carried out by, for example, the following scheme, using 5-chloro-2,3,4-trifluorobenzoyl fluoride as the starting material.

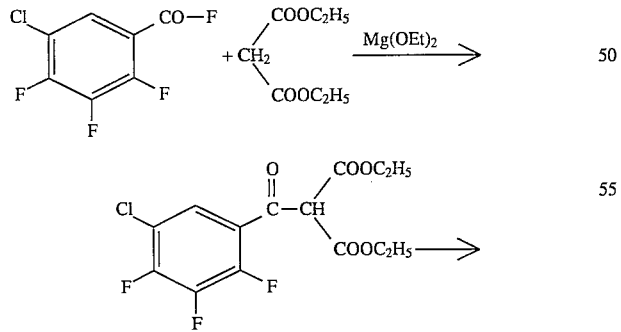

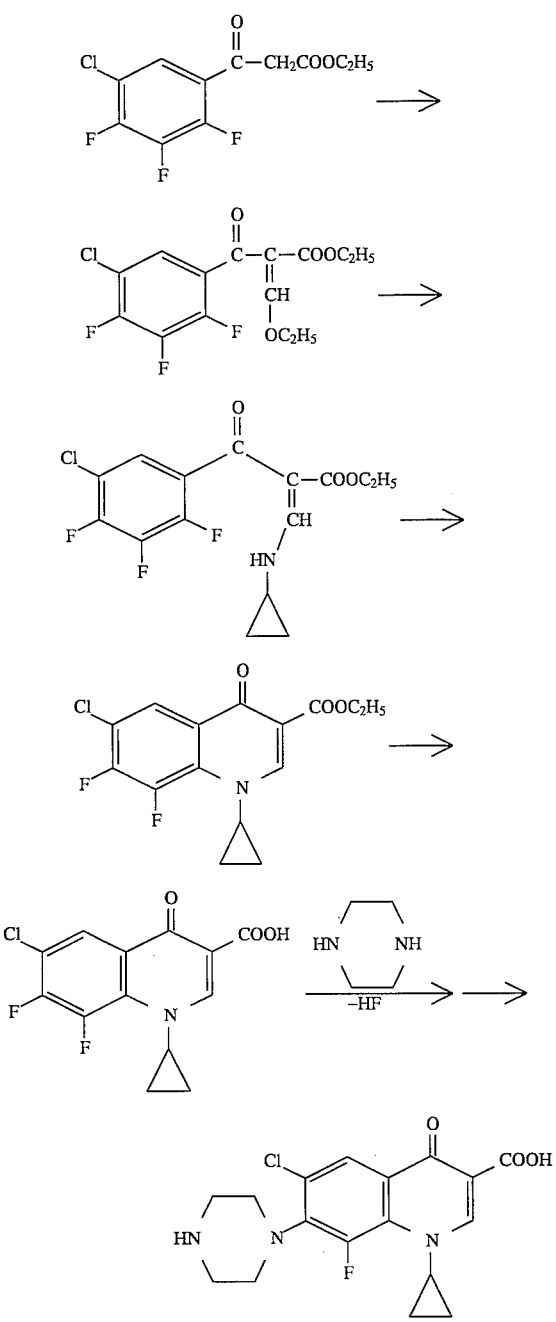

More precisely and in detail the compounds obtainable by conversion of the compounds according to the present invention are described in the following.

The compounds which are not subject matter of the present invention are new 7-amino-1-cyclopropyl-6,8-dihalogeno-1,4-dihydro-4-oxo-3-quinolinecarboxylic acids of the formula (I').

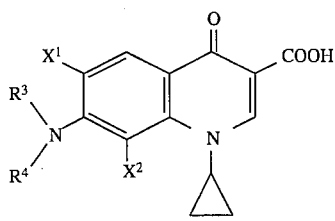

in which

X¹ and X², which can be identical or different, represent chlorine or fluorine, but cannot both be fluorine, and R³ and R⁴, together with the nitrogen atom to which they are bonded, form a 5- or 6-membered heterocyclic ring which can contain in addition, as ring member, the atoms or groups, —O—, —S—, —SO—, —SO₂—, >N—R⁵ or

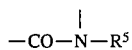

and which can optionally be substituted on the carbon atoms once to three times by $C_1$–$C_4$-alkyl, phenyl or cyclohexyl, each of which is optionally substituted once to three times by chlorine, fluorine, bromine, methyl, phenyl, hydroxy, methoxy, benzyloxy, nitro or piperidino, 2-thienyl, hydroxyl, alkoxy having 1 to 3 carbon atoms, amino, methylamino or ethylamino, R⁵ representing hydrogen, a branched or unbranched alkyl, alkenyl or alkinyl group having 1 to 6 carbon atoms which can optionally be substituted by one or two hydroxyl, alkoxy, alkylamino or dialkylamino groups having 1 to 3 carbon atoms for an alkyl radical, the cyano group, or the alkoxycarbonyl group having 1 to 4 carbon atoms in the alcohol moiety, a phenylalkyl group which is optionally substituted in the phenyl radical and has up to 4 carbon atoms in the aliphatic moiety, a phenacyl radical which is optionally substituted once or twice by hydroxyl, methoxy, chlorine or fluorine, or an oxoalkyl radical having up to 6 carbon atoms, furthermore denoting a radical COR⁶, CN or SO₂R⁷, R⁶ representing hydrogen, straight-chain or branched alkyl which has 1 to 4 carbon atoms and is optionally substituted by 1 or 2 substituents from the group comprising amino, alkoxycarbonyl having 1 to 3 carbon atoms in the alkyl moiety, carboxyl or alkoxy having 1 to 3 carbon atoms, or halogen such as chlorine, bromine or fluorine, or representing alkoxy having 1 to 4 carbon atoms, amino, alkylamino or dialkylamino having 1 to 5 carbon atoms in the alkyl moiety, and R⁷ representing straight-chain or branched alkyl having 1 to 3 carbon atoms, and their pharmaceutically utilisable hydrates, acid addition salts, alkali metal, alkaline earth metal and guanidinium salts, which have high antibacterial activity.

They are suitable as active compounds for human and veterinary medicine, veterinary medicine also including treatment of fish for the therapy or prevention of bacterial infections.

Preferred compounds of the formula (I') are those in which

X¹ and X², which can be identical or different, represent chlorine or fluorine, but cannot both be fluorine, and R³ and R⁴, together with the nitrogen atom to which they are bonded, can form a 5- or 6-membered heterocyclic ring which can contain in addition, as ring member, the atoms or groups —O—, —S—, —SO₂—, N—R³ or

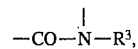

and which can optionally be substituted on the carbon atoms once to twice by $C_1$–$C_3$-alkyl, cyclohexyl, phenyl which is optionally substituted once or twice by chlorine, fluorine, bromine, methyl, phenyl, hydroxyl, methoxy, benzyloxy, nitro or piperidino, 2-thienyl, hydroxyl, amino or methylamino, R⁵ representing hydrogen, a branched or unbranched alkyl, alkenyl or alkinyl group having 1 to 4 carbon atoms, which can optionally be substituted by one or two hydroxyl groups, or a phenacyl radical, an oxoalkyl radical having up to 5 carbon atoms, and representing a radical COR⁶, R⁶ denoting hydrogen, straight-chain or branched alkyl having 1 to 3 carbon atoms, alkoxy having 1 to 3 carbon atoms, amino, alkylamino or dialkylamino having 1 to 3 carbon atoms in the alkyl moiety.

Particularly preferred compounds of the formula (I') are those
in which

X¹ and X², which can be identical or different, represent chlorine or fluorine, but cannot both be fluorine, and R³ and R⁴, together with the nitrogen atom to which they are bonded, can form a 5- or 6-membered heterocyclic ring which can contain in addition, as ring member, an oxygen atom or the groups N—R⁵ or

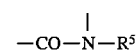

and which can optionally be substituted on the carbon atoms once to twice by $C_1$–$C_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, R⁵ representing hydrogen, a branched or unbranched alkyl group having 1 to 3 carbon atoms which can optionally be substituted by one or two hydroxyl groups, or a phenacyl radical, an oxoalkyl radical having up to 4 carbon atoms and a radical COR⁶, R⁶ denoting hydrogen or alkyl having one or two carbon atoms.

It has also been found that the compounds of the formula (I') are obtained when the 1-cyclopropyl-7-halogeno- 1,4-dihydro-4-oxo-3-quinolinecarboxylic acids of the formula (II')

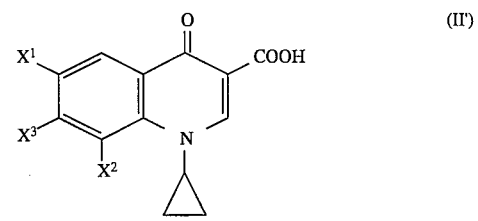

in which

X¹ and X² have the abovementioned meaning, and

X³ represents halogen, preferably chlorine or fluorine, are reacted with amines of the formula (III)

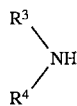
 (III)

in which

R³ and R⁴ have the abovementioned meaning, where appropriate in the presence of acid-binding agents (method A).

Compounds of the formula (I'), can also be obtained by reacting a 7-(1-piperazinyl)-3-quinolonecarboxylic acid of the formula (IV)

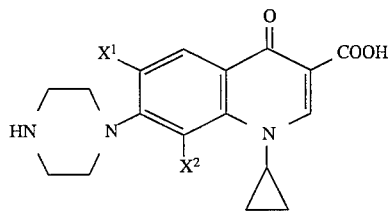
 (IV)

in which

X¹ and X² have the abovementioned meaning, and the piperazinyl radical can be substituted on the carbon atoms 1–3 times by $C_1$–$C_4$-alkyl, 2-thienyl or optionally substituted cyclohexyl or phenyl, with compounds of the formula (V)

 (V)

in which

R⁵ has the abovementioned meaning but cannot be hydrogen, and

X denotes fluorine, chlorine, bromine, iodine, hydroxyl, acyloxy, ethoxy, phenoxy or 4-nitrophenoxy, where appropriate in the presence of acid-binding agents (method B).

Compounds of the formula (I'), are also obtained when 7-(1-piperazinyl)-3-quinolonecarboxylic acid of the formula (IV), in which the piperazinyl radical can be substituted on the carbon atoms 1–3 times by $C_1$–$C_4$-alkyl, 2-thienyl or optionally substituted cyclohexyl or phenyl, is reacted with Michael acceptors of the formula (VI)

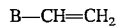 (VI)

in which

B represents CN, CO—R⁸ or COOR⁹,

R⁸ representing methyl or ethyl, and

R⁹ representing methyl, ethyl, n- or i-propyl, (method C).

When, in the reaction by method A, 2-methylpiperazine and 6-chloro-1-cyclopropyl-7,8-difluoro-1,4-dihydro-4-oxo-3-quinolinecarboxylic acid are used as starting materials, then the course of the reaction can be represented by the equation below:

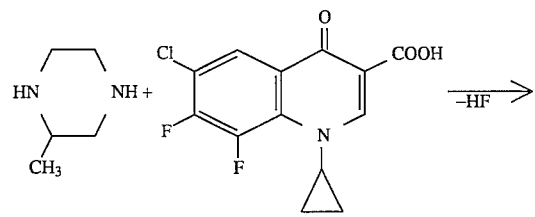

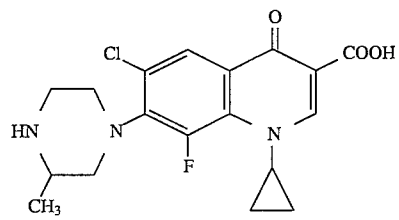

When, in the reaction by method B, ethyl iodide and 6-chloro-1-cyclopropyl-8-fluoro-1,4-dihydro-4-oxo-7-(1-piperazinyl)-3-quinolinecarboxylic acid are used as starting materials, then the course of the reaction can be represented by the equation below:

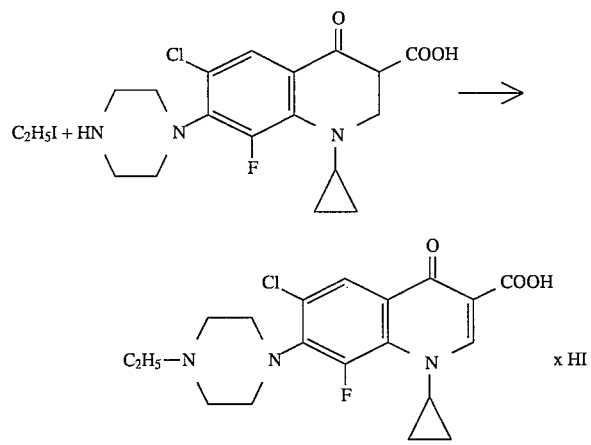

When, for example in the reaction of (IV) with (V) by method B, 6-chloro-1-cyclopropyl-8-fluoro-1,4-dihydro-7-(3-methyl-1-piperazinyl)-4-oxo-3-quinolinecarboxylic acid and formic acetic anhydride are used as starting compounds, then the course of the reaction can be represented by the equation below:

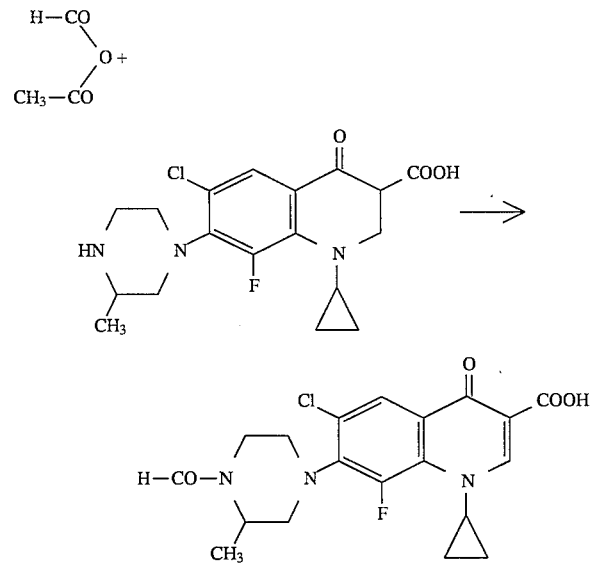

When, for example by method C, 6-chloro-1-cyclopropyl-8-fluoro-1,4-dihydro-4-oxo-7-(1-piperazinyl)-3-quinolinecarboxylic acid and methyl vinyl ketone are used as starting compounds, then the course of the reaction can be represented by the equation below:

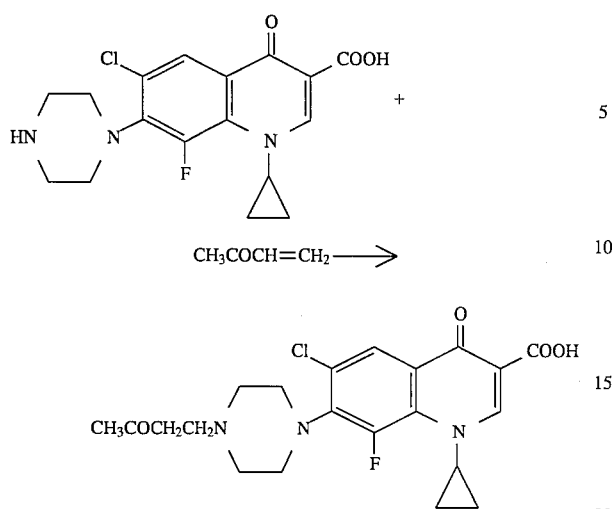

The 1-cyclopropyl-6,7,8-trihalogeno-1,4-dihydro-4-oxo-3-quinolinecarboxylic acids of the formula (II') which can be used as starting materials by method A can be prepared in accordance with the following reaction scheme:

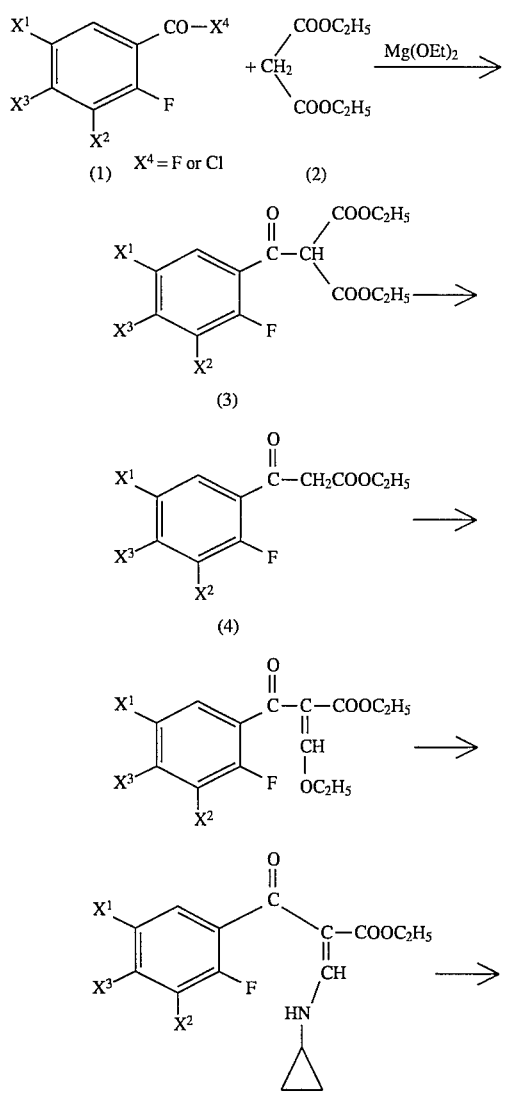

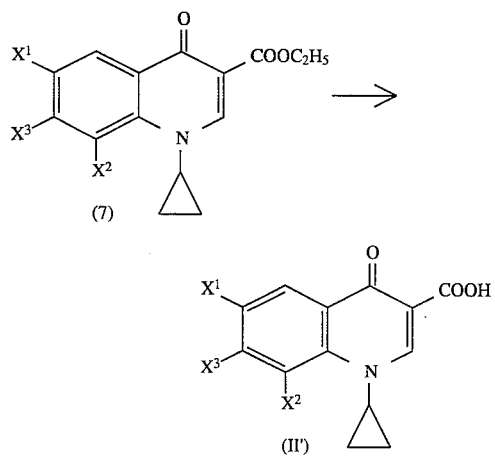

According to this, diethyl malonate (2) is acylated with the appropriate benzoyl fluoride or chloride (1), in the presence of magnesium ethylate, to give the aroylmalonic ester (3) (Organicum, 3rd edition, 1964, page 438).

By partial hydrolysis and decarboxylation of (3) in aqueous medium using catalytic amounts of sulphuric acid or p-toluenesulphonic acid, the ethyl aroylacetates (4) are obtained in good yield, and these are converted with triethyl orthoformate/acetic anhydride into ethyl 2-(2,3,4,5-tetrahalogenobenzoyl)-3-ethoxyacrylates (5). The reaction of (5) with cyclopropylamine in a solvent such as, for example, methylene chloride, alcohol, chloroform, cyclohexane or toluene leads, in a slightly exothermic reaction, to the desired intermediate (6).

The cyclisation reaction (6)→(7) is carried out in a temperature range of about 60° to 300° C., preferably 80° to 180° C.

The diluents which can be used are dioxane, dimethyl sulphoxide, N-methylpyrrolidone, sulpholane, hexamethylphosphoric trisamide and, preferably, N,N-dimethylformamide.

Suitable acid-binding agents for this reaction step are potassium tert.-butanolate, butyllithium, lithiumphenyl, phenyl magnesium bromide, sodium methylate, sodium hydride, sodium or potassium carbonate and, particularly preferably, potassium or sodium fluoride. It can be advantageous to use an excess of 10 mol-% of base.

The ester hydrolysis of (7) carried out in the last step under basic or acid conditions leads to the 1-cyclopropyl-6,7,8-trihalogen-1,4-dihydro-4-oxo-3-quinolinecarboxylic acids (II').

The benzoyl halides (1) used as starting materials for this synthetic route are prepared as follows: 3,5-dichloro-2,4-difluorobenzoyl fluoride (boiling point 97°/20 mbar; $n_D^{20}$= 1.5148) and 5-chloro-2,3,4-trifluorobenzoyl fluoride (boiling point (68°–70°/20 mbar; $n_D^{20}$= 1.4764) are obtained together by heating tetrachlorobenzoyl chloride with potassium fluoride in sulpholane at elevated temperatures:

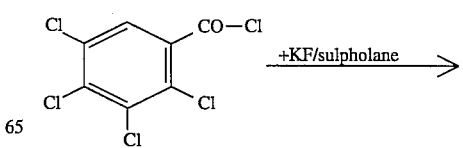

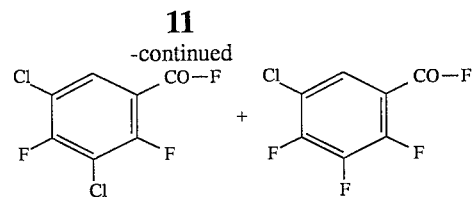

The chlorination of 2,4,5-trifluorobenzoic acid in chlorosulphonic acid leads to 3-chloro-2,4,5-trifluorobenzoic acid which is reacted as the crude product with thionyl chloride to give 3-chloro-2,4,5-trifluorobenzoyl chloride (boiling point 94°/18 mbar; $n_D^{20}$=1.5164):

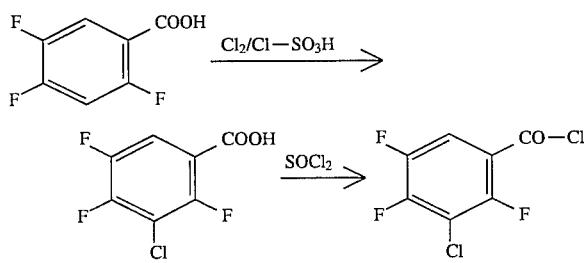

The amines (III) used as starting materials are known or can be obtained by processes known from the literature [U.S. Pat. No. 4,166,180, J. Med. Chem. 26, 1116 (1983). From the 2-arylpiperazines, the corresponding 2-cyclohexylpiperazines are obtained by catalytic hydrogenation; for example: 2-cyclohexylpiperazine (waxlike, melting point 71°–73° C.). Examples which may be mentioned are: morpholine, piperidine, thiomorpholine, pyrrolidine, piperazine, N-methylpiperazine, N-ethylpiperazine, N-(2-hydroxyethyl)piperazine, N-formylpiperazine, 2-methylpiperazine, 1,2-dimethylpiperazine, cis- and trans- 2,5-dimethylpiperazine, cis- and trans-2,6-dimethylpiperazine, 2-ethylpiperazine, 2-propylpiperazine, 2-isopropylpiperazine, 2-isobutylpiperazine, 2-piperazinone, 1-methyl- 2-piperazinone, 1-ethyl-2-piperazinone, 2-cyclohexylpiperazine, 2-phenylpiperazine, 2-(4-chlorophenyl)piperazine, 2-(4-fluorophenyl)piperazine, 2-(4-bromophenyl)piperazine, 2-(4-methylphenyl)piperazine, 2-(4-biphenylyl)-piperazine. 2-(4-methoxyphenyl)piperazine, 2-(4-benzyloxyphenyl)piperazine, 2-(4-hydroxyphenyl)piperazine, 2-(4-nitrophenyl)piperazine, 2-(3-nitrophenyl)piperazine, 2-(4-piperidinophenyl)piperazine, 2-(3,4-dimethoxyphenyl)piperazine, 2 -(3,4,5-trimethoxyphenyl)piperazine, 2-(3,4-dimethoxy-6-methyl)piperazine, 2-(2-thienyl)piperazine and 3-aminopyrrolidine.

The compounds of the formula (V) which are used as starting materials are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride and n-hexyl bromide, formic acetic anhydride, acetic anhydride, propionic anhydride, acetyl chloride, chloroacetyl chloride, onic anhydride, acetyl chloride, chloroacetyl chloride, dichloroacetyl chloride, bromoacetyl bromide, butyryl chloride, 4-chlorobutyryl chloride, isobutyryl chloride, 4 -nitrophenyl ester of N-(tert.-butoxycarbonyl)-glycine, 4 -nitrophenyl ester of N-(tert.-butoxycarbonyl)-L-alanine, 4-nitrophenyl ester of N-(tert.-butoxycarbonyl)-L-leucine, 4-nitrophenyl ester of N-(tert.-butoxycarbonyl)-L-valine, 3-methoxypropionyl chloride, methyl chlorocarbonate, ethyl chlorocarbonate, n-butyl chlorocarbonate, diethyl carbonate, cyanogen chloride, diphenyl carbonate, cyanogen bromide, dimethylcarbamoyl chloride, methanesulphonyl chloride, ethanesulphonyl chloride, propane-1-sulphonyl chloride and formic acid.

The compounds of the formula (VII) which can be used according to the invention are known. Examples which may be mentioned are: acrylonitrile, methyl vinyl ketone, methyl acrylate and ethyl acrylate.

The reaction of (II') with (III) by method A is preferably carried out in a diluent such as dimethyl sulphoxide, N,N-dimethylformamide, hexamethylphosphoric trisamide, sulpholane, water, an alcohol, such as methanol, ethanol, n-propanol, isopropanol or glycol monomethyl ether, or pyridine. It is equally possible to use mixtures of these solvents.

All customary inorganic and organic acid-binding agents can be used as the acid-binding agent. These preferably include the alkali metal hydroxides, alkali metal carbonates, organic amides and amidines. The following may be specifically mentioned as being particularly suitable: triethylamine, 1,4-diazabicyclo[2.2.2]octaine (DABCO), 1,8-diazabicyclo[5.4.0]undec-7-ene (DBU) or excess amine (III).

The reaction temperatures can be varied within a relatively wide range. In general, the process is carried out between about 20° and 200° C. preferably between 80° and 180° C.

The reaction can be carried out under atmospheric pressure as well as under elevated pressure. In general, it is carried out under pressures between about 1 and about 100 bar, preferably between 1 and 10 bar.

When carrying out the process according to the invention, 1 to 15 moles, preferably 1 to 6 moles, of the amine (III) are used for 1 mole of carboxylic acid (II').

The reaction of (IV) with (V) is preferably carried out in a diluent such as dimethyl sulphoxide, dioxane, N,N-dimethylformamide, hexamethylphosphoric trisamide, sulpholane, water, an alcohol, such as methanol, ethanol, n-propanol, isopropanol or glycol monomethyl ether, or pyridine. It is equally possible to use mixtures of these diluents.

All customary inorganic and organic acid-binding agents can be used as the acid-binding agent. These preferably include the alkali metal hydroxides, alkali metal carbonates, organic amines and amidines. The following may be specifically mentioned as being particularly suitable: triethylamine, 1,4-diazabicyclo[2.2.2]octane (DABCO) or 1,8-diazabicyclo[5.4.0]undec-7-ene (DBU).

The reaction temperatures can be varied within a relatively wide range. In general, the process is carried out between about 20° and about 180° C., preferably between 40° and 110° C.

The reaction can be carried out under atmospheric pressure as well as under elevated pressure. In general, it is carried out under pressures between about 1 and about 100 bar, preferably between 1 and 10 bar.

When carrying out the process according to the invention by method B, 1 to 4 moles, preferably 1 to 1.5 mole, of the compound (V) is used for 1 mole of the compound (IV).

The reaction of (IV) with (VI) (method C) is preferably carried out in a diluent such as dioxane, dimethyl sulphoxide, N,N-dimethylformamide, methanol, ethanol, isopropanol, n-propanol or glycol monomethyl ether or in mixtures of these diluents.

The reaction temperatures can be varied within a relatively wide range. In general, the process is carried out between about 20° C. and about 150° C., preferably between 50° C. and 100° C.

The reaction can be carried out under atmospheric pressure as well as under elevated pressure. In general, it is carried out under pressures between about 1 and about 100 bar, preferably between 1 and 10 bar.

When carrying out the process according to the invention by method C, 1 to 5 moles, preferably 1 to 2 moles, of the compound (VI) are used for 1 mole of the compound (IV).

Apart from the compounds listed in the examples, the following may be specifically mentioned as active compounds obtainable from the compounds of the invention: 6-chloro-7-[3-(4-chlorophenyl)-1-piperazinyl]- 1-cyclopropyl-8-fluoro-1,4-dihydro-4-oxo-3-quinolinecarboxylic acid, 6-chloro-1-cyclopropyl-8-fluoro-7-[3-(4-fluorophenyl)-1-piperazinyl]-1,4-dihydro-4-oxo-3-quinolinecarboxylic acid, 7-[3-(4-bromophenyl)-1-piperazinyl]-6-chloro-1 -cyclopropyl-8-fluoro-1,4-dihydro-4-oxo-3-quinolinecarboxylic acid, 6-chloro-1-cyclopropyl-8-fluoro-1,4-dihydro-7 -[3-(4-methylphenyl)-1-piperazinyl]-4-oxo-3-quinolinecarboxylic acid, 7-[3-(4-biphenylyl)-1-piperazinyl]-6-chloro-1 -cyclopropyl-8-fluoro-1,4-dihydro-4-oxo-3-quinolinecarboxylic acid, 6-chloro-1-cyclopropyl-8-fluoro-1,4-dihydro-7 -[3-(4-methoxyphenyl)-1-piperazinyl]-4-oxo-3-quinolinecarboxylic acid, 6-chloro-1-cyclopropyl-8-fluoro-1,4-dihydro- 7-[3-(4-hydroxyphenyl)-1-piperazinyl]-4-oxo-3-quinolinecarboxylic acid, 8-chloro-1-cyclopropyl-6-fluoro-1,4-dihydro- 4-oxo-7-(3-phenyl-1-piperazinyl)-3-quinolinecarboxylic acid, 8-chloro-1-cyclopropyl-6-fluoro-1,4-dihydro-4-oxo- 7-[(4-nitrophenyl)-1-piperazinyl]-3-quinolinecarboxylic acid, 8-chloro-1-cyclopropyl-6-fluoro-1,4-dihydro-4-oxo- 7-[3-(4-piperidino-phenyl)-1-piperazinyl]-3-quinolinecarboxylic acid, 8-chloro-1-cyclopropyl-6-fluoro-1,4-dihydro-4 -oxo-7-[3-(3,4-dimethoxy-phenyl)-1-piperazinyl]-3-quinolinecarboxylic acid, 8-chloro-1-cyclopropyl-6-fluoro-1,4-dihydro- 4-oxo-7-[3-(3,4,5-trimethoxy-phenyl)-1-piperazinyl]-3-quinolinecarboxylic acid, 8-chloro-1-cyclopropyl-6-fluoro- 1,4-dihydro-4-oxo-7-[3-(2-thienyl)-1-piperazinyl]-3-quinolinecarboxylic acid, 8-chloro-1-cyclopropyl-6-fluoro-1,4 -dihydro-4-oxo-7-piperidino-3-quinolinecarboxylic acid, 7-(3-amino-1-pyrrolidinyl)-8-chloro-1-cyclopropyl-6-fluoro- 1,4-dihydro-4-oxo-3-quinolinecarboxylic acid, 6,8-dichloro- 1-cyclopropyl-1,4-dihydro-4-oxo-7-(1-piperazinyl)-3-quinolinecarboxylic acid, 7-(4-acetyl-1-piperazinyl)-6,8-dichloro- 1-cyclopropyl-1,4-dihydro-4-oxo-3-quinolinecarboxylic acid, 7-(4-acetyl-1-piperazinyl)-6-chloro-1-cyclopropyl- 8-fluoro-1,4-dihydro-4-oxo-3-quinolinecarboxylic acid, 6-chloro-1-cyclopropyl-8-fluoro-1,4-dihydro-7-(4 -isopropyl-1-piperazinyl)-4-oxo-3-quinolinecarboxylic acid, 6-chloro-1-cyclopropyl-8-fluoro-1,4-dihydro-4-oxo-7 -morpholino-3-quinolinecarboxylic acid, 6-chloro-1-cyclopropyl- 8-fluoro-1,4-dihydro-4-oxo-7-thiomorpholino-3-quinolinecarboxylic acid and 8-chloro-1-cyclopropyl-7-(4-ethyl- 3-oxo-1-piperazinyl)-6-fluoro-1,4-dihydro-4-oxo-3-quinolinecarboxylic acid.

The examples which follow shall illustrate end products obtainable from compounds which are subject matter of the present invention.

EXAMPLE A

6-Chloro-1-cyclopropyl-7,8-difluoro-1,4-dihydro-4-oxo-3-quinolinecarboxylic acid

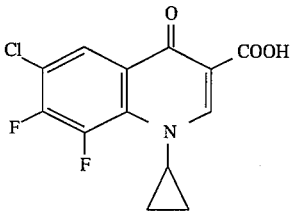

15.7 g (0.65 mole) of magnesium turnings are stirred in 40 ml of ethanol and 2 ml of tetrachloromethane and, after the reaction has started, 103 g (0.64 mole) of diethyl malonate in 80 ml of ethanol and 250 ml of toluene are added dropwise at 50°–60°. The mixture is stirred at this temperature for 1 hour, cooled to −5° to −10°, a solution of 138 g (0.65 mole) of 5-chloro-2,3,4-trifluoro-benzoyl fluoride in 63 ml of toluene is added dropwise, and the mixture is stirred further at 0° for 1 hour and allowed to stand overnight at room temperature. It is then heated at 40°–50° for 2 hours, cooled, and 250 ml of ice-water and 38.5 ml of concentrated sulphuric acid are added. The organic phase is separated off, the aqueous phase is extracted with 2×150 ml of toluene, and the combined organic phases are washed with saturated sodium chloride solution, dried with sodium sulphate and concentrated.

200 ml of water are added to the residue (it is advantageous to add 0.4 g of 4-toluenesulphonic acid at this point) and the mixture is heated under reflux for 5 hours for the deethoxycarbonylation. The mixture is extracted with 3×200 ml of dichloromethane, and the extracts are washed with saturated sodium chloride solution, dried with sodium sulphate, concentrated and distilled under high vacuum. 103 g (56.5%) of ethyl (5 -chloro-2,3,4-trifluorobenzoyl)-acetate with a boiling point of 110°/0.9 Torr are obtained.

103 g (0.37 mole) of the ester obtained and 83 g (0.56 mole) of triethyl orthoformate are heated with 95 g of acetic anhydride at 150°–160° for 2 hours and then concentrated at 120°–130° under atmospheric pressure and thereafter under high vacuum. 115 g (92% of theory) of ethyl (2-(5-chloro-2,3,4-trifluorobenzoyl)-3-ethoxyacrylate are obtained as an oil.

14.8 g (0.26 mole of cycloproplamine are added dropwise to 84.1 g (0.25 mole) of this compound in 170 ml of ethanol, cooling in ice, and the mixture is stirred at room temperature for 2 hours. It is then stirred with 170 ml of water, cooled in ice, and the precipitate which has separated out is filtered off with suction, washed with water and a little methanol and dried. 47 g (54%) of ethyl 2-(5-chloro-2,3,4-trifluorobenzoyl)-3-cyclopropylaminoacrylate of melting point 71°–73° are obtained. The product is a cis/trans mixture according to the $^1$H NMR spectrum.

47 g (0.14 mole) of this compound in 230 ml of dimethylformamide are heated with 9.7 g (0.23 mole) of sodium fluoride at 160°–170° for 2 hours. The reaction mixture is poured into 400 ml of ice-water, and the precipitate is filtered off with suction, washed with water and dried. 44 g (99% of ethyl 6-chloro-1-cyclopropyl- 7,8-difluoro-1,4-dihydro-4-oxo-3-quinolinecarboxylate of melting point 169°–172° are isolated.

33 ml of concentrated sulphuric acid are added to 44 g (0.13 mole) of the quinolonecarboxylic ester in 300 ml of glacial acetic acid and 179 ml of water and the reaction mixture is heated at 150° C. for 2 hours. It is stirred into 400 ml of ice-water, and the precipitate is filtered off with suction, washed with water and dried. 37 g (95% of theory) of 6-chloro-1-cyclopropyl-7,8-difluoro-1,4-dihydro- 4-oxo-3-quinolinecarboxylic acid isolated with a melting point of 200°–204°.

EXAMPLE B

8-Chloro-1-cyclopropyl-6,7-difluoro-1,4-dihydro-4-oxo-3-quinolinecarboxylic acid

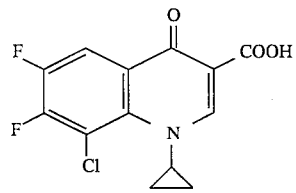

3-Chloro-2,4,5-trifluorobenzoyl chloride is reacted in analogy to Example A, the following steps being passed through: ethyl (3-chloro-2,4,5-trifluorobenzoyl)acetate as the enol (yield: 42%, melting point 72–75), ethyl 2-(3-chloro-2,4,5-trifluorobenzoyl)-3-ethoxyacrylate (crude yield: 95% oil), ethyl 2-(3-chloro-2,4,5-trifluorobenzoyl)-3-cyclopropylaminoacrylate (yield: 67%, melting point 78°–80°), ethyl 8-chloro-1-cyclopropyl-6,7-difluoro-1,4-dihydro- 4-oxo-3-quinolinecarboxylate (yield: 85%, melting point 154°–157°), 8-chloro-1-cyclopropyl-6,7-difluoro- 1,4-dihydro-4-oxo-3-quinolinecarboxylic acid (yield: 97.6%, melting point 189°–192°).

EXAMPLE C 6,8-Dichloro-1-cyclopropyl-7-fluoro-1,4-dihydro-4-oxo-3-quinolinecarboxylic acid

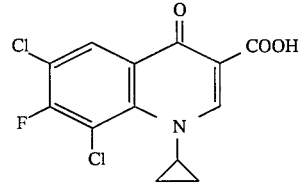

3,5-Dichloro-2,4-difluorobenzoyl fluoride is reacted in analogy to Example A, the following steps being passed through: ethyl (3,5-dichloro-2,4-difluorobenzoyl)acetate (yield: 43%, melting point 133°/2.5 Torr), ethyl 2-(3,5-dichloro- 2,4-difluorobenzoyl)-3-ethoxyacrylate (crude yield: 95% oil), ethyl 2(3,5-dichloro-2,4-difluorobenzoyl)-3-cyclopropylaminoacrylate (yield: 96%, melting point 71°–74°), ethyl 6,8-dichloro-1-cyclopropyl-7-fluoro-1,4-dihydro-4 -oxo-3-quinolinecarboxylate (yield: 97%, melting point 215°–217° with decomposition), 6,8-dichloro-1-cyclopropyl- 7-fluoro-1,4-dihydro-4-oxo-3-quinolinecarboxylic acid (yield: 93%, melting point 204°–206°).

EXAMPLE 1

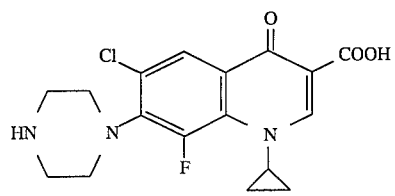

12 g (40 mmol) of the product from Example A in 100 ml of pyridine are heated with 17.2 g (0.2 mole) of piperazine under reflux for 5 hours. The mixture is concentrated in vacuo, the residue is stirred with 120 ml of water and the pH is adjusted to 5 with 2N hydrochloric acid. The precipitate is filtered off with suction, washed with water and methanol, boiled in 80 ml of methanol and dried. 12.3 g (84% of theory) 6-chloro-1 -cyclopropyl-8-fluoro-1,4-dihydro-4-oxo-7-(1-piperazinyl)- 3-quinolinecarboxylic acid of melting point 295°–298° (with decomposition) are obtained.

The following 6-chloro-1-cyclopropyl-8fluoro-1,4 -dihydro-4-oxo-3-quinolinecarboxylic acids substituted in the 7-position are obtained in analogy to Example 1:

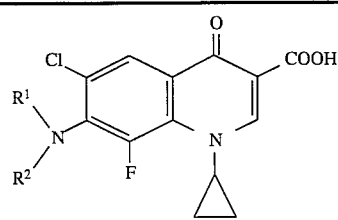

| Example | $\begin{array}{c}R^1\\ \diagdown\\ N-\\ \diagup\\ R^2\end{array}$ | Melting point |
|---|---|---|
| 2 | HN⌒N— with CH₃ | 258–282° (decomposition) |
| 3 | HN⌒N— with C₂H₅ | 191–195° (decomposition) |
| 4 | HN⌒N— with H₃C CH₃ | above 274° (decomposition) |
| 5 | CH₃ HN⌒N— CH₃ | 255–261° (decomposition) |

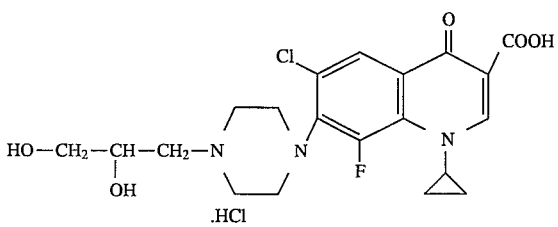

| Example | $R^1, R^2$ N— | Melting point |
|---|---|---|
| 6 | H₃C—N⏝N— .HCl | >320° (decomposition) |
| 7 | HO—CH₂CH₂—N⏝N— | 276–280° (decomposition) |
| 8 | HN⏝N— CH₂—cyclohexyl | above 190° (decomposition) |
| 9 | HN⏝N— CH₂—phenyl | 154–158 |

EXAMPLE 10

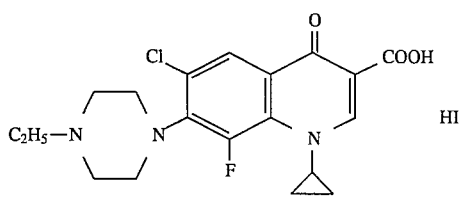

1.83 g (5 mmol) of the product from Example 1 in 20 ml of dimethylformamide are heated with 1.6 g of ethyl iodide and 1 g of triethylamine at 80° for 3 hours. The reaction mixture is concentrated in vacuo, and the residue is stirred with 20 ml of water and recrystallised from methanol. 0.4 g (15% of theory) of 6-chloro-1-cyclopropyl- 7-(4-ethyl-1-piperazinyl)-8-fluoro-1,4-dihydro-4-oxo-3 -quinolinecarboxylic acid of melting point 237°–242° (with decomposition) is obtained.

EXAMPLE 11

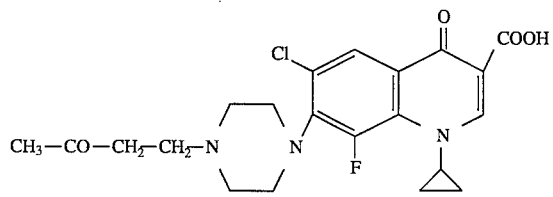

3.65 g (0.01 mmol) of the product from Example 1 are suspended in 150 ml of ethanol and 30 ml of water, the suspension is adjusted to pH 4.6 with acetic acid, and then, at room temperature, 3.4 g (0.02 mol) of 2,3-cyclohexylideneglyceraldehyde and, in portions, 950 mg of sodium cyanoborohydride are added. The mixture is stirred at room temperature overnight, the pH is adjusted to 8 with sodium bicarbonate, extraction with dichloromethane is carried out, and the extract is concentrated. 3 ml of concentrated hydrochloric acid are added to the residue in 25 ml of ethanol and 25 ml of water, and the mixture is heated under reflux for 6 hours. It is concentrated, the residue is dissolved in water, the solution is extracted with dichloromethane, concentration is again carried out, and the residue is stirred with ethanol and dried. 1.3 g of 6-chloro-1-cyclopropyl-8-fluoro-1,4-dihydro-7-[4-(2,3 -dihydroxypropyl)-1-piperazinyl]-4-oxo-3-quinolinecarboxylic acid hydrochloride of melting point 263°–266° (with decomposition) is obtained.

EXAMPLE 12

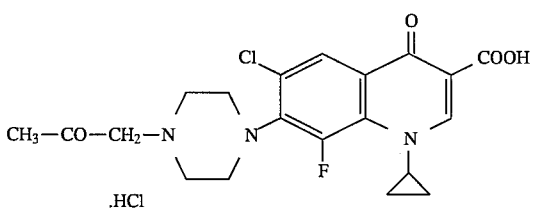

1.83 g (5 mmol) of the product from Example 1 and 1.95 g (28 mmol) of methyl vinyl ketone in 25 ml of ethanol are heated under reflux for 6 hours, and the precipitate is filtered off with suction and recrystallised from glycol monomethyl ether. 1 g (46% of theory) of 6-chloro-1-cyclopropyl-8-fluoro-1,4-dihydro-4-oxo-7-[4-(3-oxobutyl)-1 -piperazinyl]-3-quinolinecarboxylic acid of melting point 187°–190° (with decomposition) is obtained.

EXAMPLE 13

1.83 g (5 mmol) of the product from Example 1 in 25 ml of ethanol are heated with 1.95 g (20 mmol) of chloroacetone under reflux for 6 hours. The suspension is cooled, and the precipitate is filtered off with suction, thoroughly washed with ethanol and dried in vacuo, 1 g (44% of theory) of 6-chloro-1-cyclopropyl-8-fluoro-1,4-dihydro-4-oxo-7-[4-(2-oxopropyl)-1-piperazinyl]-3-quinolinecarboxylic acid hydrochloride of melting point ~320° C. (with decomposition) being obtained.

EXAMPLE 14

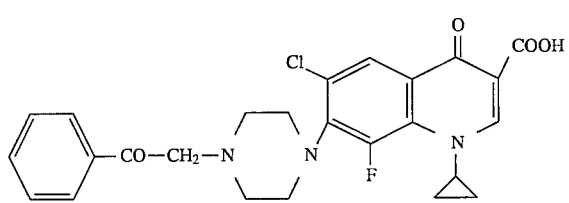

3.66 g (0.01 mole) of the product from Example 1 in 50 ml of dimethylformamide are heated with 2.2 g of ω-chloroacetophenone and 2.2 g of triethylamine at 60° for 10 hours. The reaction mixture is concentrated in vacuo, the residue is stirred with 30 ml of water, and the precipitate is filtered off with suction, washed with water and recrystallised from acetone. 1.2 g (25% of theory) of 6-chloro-1-cyclopropyl-8-fluoro-1,4-dihydro-4-oxo-7-[4-(2-oxo-2-phenylethyl)-1-piperazinyl]-3-quinolinecarboxylic acid of melting point 175°–179° (with decomposition) is obtained.

EXAMPLE 15

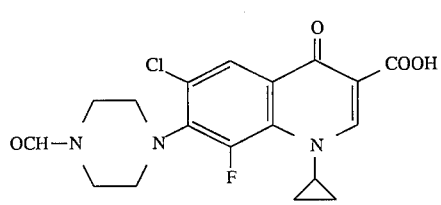

1.5 g (4 mmol) of the product from Example 1 are dissolved in a mixture of 10 ml of dioxane and 170 mg of sodium hydroxide in 2.5 ml of water and then, simultaneously, a solution of 0.7 g of formic acetic anhydride in 5 ml of dioxane and a solution of 340 mg of sodium hydroxide in 5 ml of water are added. The mixture is stirred at room temperature for 2 hours, diluted with 30 ml of water, and the precipitate is filtered off with suction, washed with water and recrystallised from glycol monomethyl ether. 0.6 g (38%) of 6-chloro-1-cyclopropyl-8-fluoro-7(4-formyl-1-piperazinyl)-1,4-dihydro-4-oxo-3 quinolinecarboxylic acid of melting point 277°–278° (with decomposition) is obtained.

EXAMPLE 16

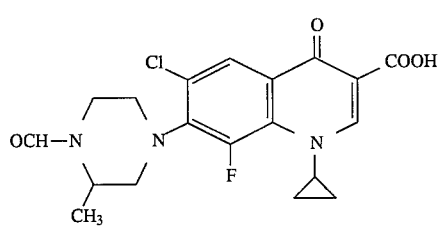

When the product from Example 2 is reacted in analogy to Example 15, then 6-chloro-1-cyclopropyl-8-fluoro-7(4-formyl-3-methyl-1-piperazinyl)-1,4-dihydro-4-oxo-3-quinolinecarboxylic acid of melting point 280°–282° (with decomposition) is obtained.

EXAMPLE 17

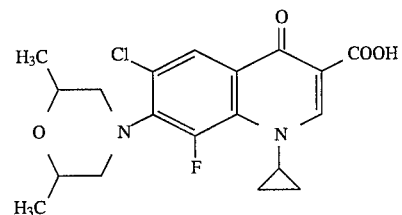

3 g (10 mmol) of the product from Example A in 35 ml of dimethyl sulphoxide are heated at 140° with 1.2 g (10 mmol) of 2,6-dimethylmorpholine and 2.2 g (20 mmol) of diazabicyclo[2.2.2]octane for 5 hours. The mixture is concentrated under high vacuum, stirred with 30 ml of water, the pH is adjusted to 6 with 2N hydrochloric acid, and the precipitate is filtered off with suction and recrystallised from glycol monomethyl ether. 1.6 g (41% of theory) of 6-chloro-1-cyclopropyl-8-fluoro-1,4-dihydro-7-(2.6-dimethyl-4-morpholinyl)-4-oxo-3-quinolinecarboxylic acid of melting point 258°–261° (with decomposition) is obtained.

EXAMPLE 18

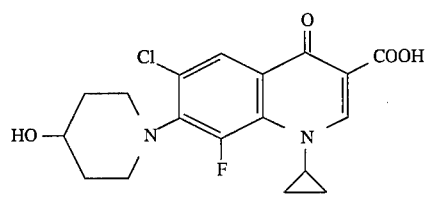

When the product from Example A is reacted with 4-hydroxypiperidine in analogy to Example 17, then 6-chloro-1-cyclopropyl-8-1,4-dihydro-7-(4-hydroxy-1-piperidinyl)-4-oxo-3-quinolinecarboxylic acid of melting point 226°–231° (with decomposition) is obtained.

EXAMPLE 19

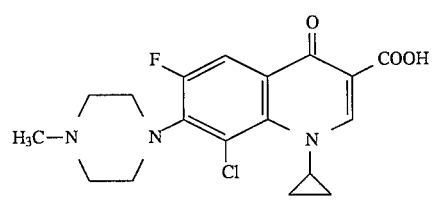

3 g (0.01 mole) of the product from Example B in 25 ml of pyridine are heated with 4 g (0.04 mole) of 1-methylpiperazine under reflux for 5 hours. The mixture is concentrated in vacuo, 20 ml of water are added, the pH is adjusted to 5 with 2N hydrochloric acid, and the precipitate which has separated out is recrystallised from methanol. 0.6 g (16% of theory) of 8-chloro-1-cyclopropyl-6-fluoro-1,4-dihydro-7-(4-methyl-1-piperazinyl)-4-oxo-3-quinolinecarboxylic acid of melting point 293°–297° (with decomposition) is obtained.

EXAMPLE 20

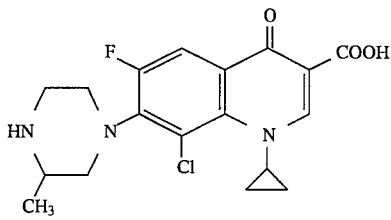

In analogy to Example 19, with 2-methylpiperazine, 8-chloro-1-cyclopropyl-6-fluoro-1,4-dihydro-7-(3-methyl-1-piperazinyl)-4-oxo-3-quinolinecarboxylic acid of melting point 318°–325° (with decomposition) is obtained.

EXAMPLE 21

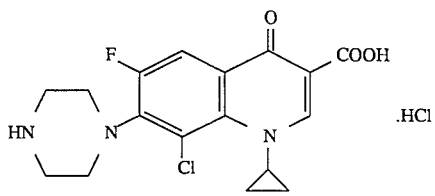

In analogy to Example 19, the product from Example B is reacted with piperazine under reflux for 1.5 hours, and the reaction mixture is treated with hydrochloric acid, 8-chloro-1-cyclopropyl-6-fluoro-1,4-dihydro-7-(1-piperazinyl)-3-quinolinecarboxylic acid hydrochloride with a decomposition point above 330° being obtained.

EXAMPLE 22

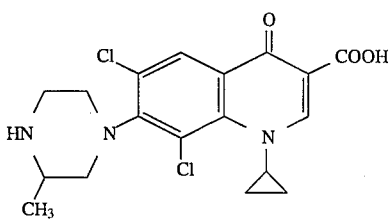

When the product from Example C is reacted with 2-methylpiperazine in analogy to Example 19, then 6,8-dichloro-1-cyclopropyl-1,4-dihydro-7-(3-methyl-1-piperazinyl)-4-oxo-3-quinolinecarboxylic acid of melting point 288°–291° (with decomposition) is obtained.

EXAMPLE 23

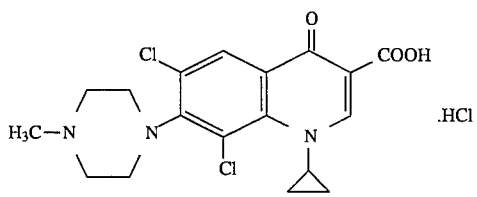

3.2 g (0.01 mole) of the product from Example C are heated with 4 g (0.04 mole) of 1-methylpiperazine at 80° for 3 days, the reaction mixture is concentrated in vacuo, and the residue is taken up in a little water and the pH is adjusted to 7 with 2N hydrochloric acid. Crystallisation takes place on standing in ice. The precipitate was filtered off with suction and recrystallised from water with the addition of a little hydrochloric acid. 0.6 g 6,8-dichloro-1-cyclopropyl-1,4-dihydro-7-(4-methyl-1-piperazinyl)-4-oxo-3-quinolinecarboxylic acid of melting point >300° is obtained.

EXAMPLE 24

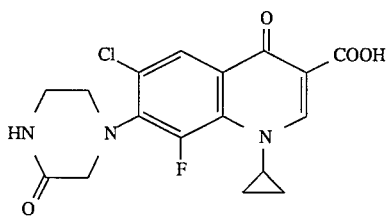

3 g (10 mmol) of the product from Example 1 in 25 ml of dimethyl sulphoxide are heated with 1.8 g (18 mmol) of 2-piperazinone and 2.2 g (20 mmol) of diazabicyclo[2.2.2]octane at 130° for 2 hours. The suspension is adjusted to pH 5 with 2N hydrochloric acid, 25 ml of water area added, and the precipitate is filtered off with suction, extracted by boiling with 20 ml of methanol and dried. 1.5 g (39% of theory) of 6-chloro-1-cyclopropyl-8-fluoro-1,4 -dihydro-4-oxo-7-(3-oxo-1-piperazinyl)-3-quinolinecarboxylic acid of melting point 288°–291° (with decomposition) is obtained.

Examples following are examples of compounds according to the present invention:

EXAMPLE 25

2,4,5-Trifluorobenzoyl fluoride

By treating 2,4-dichloro-5-fluorobenzoylchloride (b.p. 113/14 mbar, $n_D^{20}$: 1.5722) with a 4-fold excess of anhydrous HF at 120° in an autoclave for 3 hours with the elimination of hydrogen chloride, 2,4-dichloro-5-fluorobenzoyl fluoride with a boiling point of 98° C./15 mbar, $n_D^{20}$: 1.5355, is prepared.

878 g of 2,4-dichloro-5-fluorobenzoyl fluoride are reacted, in 2,350 ml of tetramethylene sulphone in a three-necked flask with stirrer, thermometer and a distillation column, with 1,142 g of anhydrous KF at 200° C. for 3.5 hours. During this, distillate is continuously removed through the distillation column, initially at 750 mbar, and towards the end at about 80 mbar. The crude distillate is subjected to fractional redistillation. 486 g (65.5% of theory) of 2,4,5-trifluorobenzoyl fluoride, of boiling point 52°–3°/20 mbar, $n_D^{20}$: 1.4530, are obtained.

After hydrolysis of 161 g of 2,4,5-trifluorobenzoyl fluoride with a solution of 100 g of sodium hydroxide in 1 l of water at 40° (exothermic up to 70°), diluting the mixture with 1 l of water, acidifying the diluted mixture with hydrochloric acid filtering the acidified mixture and drying the product 2,4,5-trifluorobenzoic acid with a melting point of 95° C. is obtained in an almost quantitative yield.

EXAMPLE 26

Fluorination of 2,3,4,5-tetrachlorobenzoyl chloride 2,749 g of 2,3,4,5-tetrachlorobenzoyl fluoride, of melting point 52°–53° C., are obtained from 2,994 g of 2,3,4,5-tetrachlorobenzoyl chloride, of boiling point 118° C./0.5 mbar, melting point 38° C., after fluorination with 1.6 l of anhydrous hydrofluoric acid in 2.0 l of methylene chloride at 60° C. in an autoclave (5 hours), and after distillation of the HF and the solvent.

This quantity is heated together with 2,914 g of anhydrous KF in 7,250 ml of tetramethylene sulphone in a three-necked flask, and initially about 500 ml of the solvent is distilled out again to remove any residual water. The reaction mixture is then heated at 240° C., with vigorous stirring, for about 4.5 hours. During this, the initial pressure of 800 mbar is reduced continuously to 500 mbar. At the same time, the mixture of fluorination products is removed as the distillate through the fractionating column. The total obtained is 1,840 g. The following are obtained from this by fractional redistillation:

206 g of 2,3,4,5-tetrafluorobenzoyl fluoride, boiling point: 45°–7° C./20 mbar, $n_D^{20}$: 1.4372;

954 g of 5-chloro-2,3,4-trifluorobenzoyl fluoride, boiling point: 68°–70° C./20 mbar, $n_D^{20}$: 1.4764;

330 g of 3,5-dichloro-2,4-difluorobenzoyl fluoride, boiling point: 97° C./20 mbar, $n_D^{20}$: 1.5148.

64 g of 5-chloro-2,3,4-trifluorobenzoyl fluoride are heated with 13 g of SiCl$_4$ in the presence of 0.1 g of AlCl$_3$. The reaction starts at about 35° C. and is completed at a temperature of up to about 100° C., and then the residue is worked up by distillation. The following is obtained:

62 g of 5-chloro-2,3,4-trifluorobenzoyl chloride, boiling point: 88° C./14 mbar, $n_D^{20}$: 1.5146.

3,5-Dichloro-2,4-difluorobenzoyl chloride is also obtained correspondingly, as a liquid of boiling point 113°–4° C./15 mbar, $n_D^{20}$: 1.5512.

When 5-chloro-2,3,4-trifluorobenzoyl fluoride is briefly treated with aqueous sodium hydroxide solution then, after acidification and drying, crystals of 5-chloro- 2,3,4-trifluorobenzoic acid are obtained, melting point: 123°–4° C.

3,5-Dichloro-2,4-difluorobenzoic acid is obtained correspondingly, melting point: 179° C.

EXAMPLE 27

5-Chloro-2,3,4-trifluorobenzyl alcohol 62 g of NaBH$_4$ are initially introduced into 320 ml of dioxane. A solution of 319 g of 5-chloro-2,3,4 -trifluorobenzoyl fluoride in 640 ml of dioxane is run into this, at the reflux temperature, over the course of 6 hours. After boiling under reflux for a further hour, the mixture is poured into ice, the pH is adjusted to 1 with dilute hydrochloric acid, and the organic phase is extracted with methylene chloride and then distilled:

261 g of 2,3,4-trifluoro-5-chlorobenzyl alcohol of boiling point 109° C./12 mbar are obtained.

3,5-Dichloro-2,4-difluorobenzyl alcohol is obtained correspondingly, as crystals of boiling point 134° C./13 mbar, melting point: 55° C., from 3,5-dichloro- 2,4-difluorobenzoyl fluoride.

EXAMPLE 28

3-Chloro-2,4,5-trifluorobenzoyl fluoride 150 g of 2,4,5-trifluorobenzoic acid are dissolved in 150 ml of chlorosulfonic acid and, after addition of 3 g of iodine, chlorination is carried out with gaseous chlorine at 50° to 60° C. Chlorination is continued until about 35 to 50% of the starting material has been converted, and then the mixture is cautiously decomposed on ice.

The mixture of nuclear halogenated acids is filtered off with suction and dried (purification of a sample by repeated recrystallization gives a melting point of 114°–5° C. for 3-chloro-2,4,5-trifluorobenzoic acid).

The crude mixture is converted into the mixture of acid chlorides using excess thionyl chloride in the presence of a few drops of dimethylformamide. 3-Chloro- 2,4,5-trifluorobenzoyl chloride is isolated by precision distillation of a sample, boiling point 94° C./18 mbar, $n_D^{20}$: 1.5164.

100 ml of anhydrous HF are added to the remainder in a stainless steel autoclave at about −5° C. and, after the evolution of HCl has subsided, the mixture is briefly heated to 60° C. to complete the reaction and then worked up by distillation. 38 g of 3-chloro-2,4,5-trifluorobenzoyl fluoride of boiling point 65° C./18 mbar, $n_D^{20}$: 1.4760 are isolated.

3-Chloro-2,4,5-trifluorobenzyl alcohol is obtained by reduction of the acid fluoride with NaBH$_4$: boiling point 109° C./14 mbar, melting point 32° C.

39 g of 3-chloro-2,4,5-trifluorobenzyl alcohol are oxidised in 92 ml of acetone with a solution of 20 g of Na$_2$Cr$_2$O$_7$ in 81 ml of water and 14 ml of concentrated sulphuric acid for 2 hours at 20° to 25° C., the organic phase is washed with aqueous sodium carbonate solution and dried with sodium sulphate. After evaporating off the solvent and after distillation 2,4,5-trifluoro-3-chlorobenzaldehyde, b.p. 72° C./12 mbar, $n_D^{20}$: 1.5055, which crystallises slowly and has a melting point of 31°–32° C., is obtained.

EXAMPLE 29

Fluorination of 2,3,4,5-tetrachlorobenzonitrile 2,3,4,5-Tetrachlorobenzonitrile of melting point: 123°–5° C. (prepared from 2,3,4,5-tetrachlorobenzoyl chloride, melting point: 30° C., via 2,3,4,5-tetrachlorobenzamide, melting point: 206°) are fluorinated with KF in tetramethylene sulphone. The following are isolated by fractional distillation of the fluorination mixture:

2,3,4,5-tetrafluorobenzonitile, boiling point 50° C./ 15 mbar, $n_D^{20}$: 1.4562;

5-chloro-2,3,4-triflurobenzonitrile, boiling point 78° C./ 14 mbar, $n_D^{20}$ 1.4960; and 3,5-dichloro-2,4-difluorobenzonitrile, boiling point 113° C./19 mbar, melting point: 39°–40° C.

EXAMPLE 30

3,5-Dichloro-2,4-difluorobenzamide 620 ml of concentrated aqueous ammonia solution and 600 ml of water are initially introduced, 458 g (2 moles) of 3,5-dichloro-2,4-difluorobenzoyl fluoride are added dropwise at 40°–50°, and then the mixture is stirred at 50° for 30 minutes. The precipitate is filtered off with suction, washed with water and dried. 408 g (90% of theory) of 3,5-dichloro-2,4-difluorobenzamide of melting point 163°–164° are obtained.

The following are obtained analogously:
5-chloro-2,3,4-trifluorobenzamide, melting point: 135°–137°,
5-chloro-2,4,5-trifluorobenzamide, melting point: 125°,
2,4,5-trifluorobenzamide, melting point: 145°–147°, and
2,3,4,5-trifluorobenzamide, melting point: 206°.

EXAMPLE 31

3,5-Dichloro-2,4-difluorobenzyl chloride 354 ml of thionyl chloride and 1 drop of dimethylformamide are initially introduced at room temperature, and 375 g (1.76 mol) of 3,5-dichloro-2,4-difluorobenzyl alcohol are added dropwise. The mixture is heated under reflux until evolution of gas has finished. The excess thionyl chloride is removed by distillation, and the residue is distilled in vacuo. 386 g (95% of theory) of 3,5 -dichloro-2,4-difluorobenzyl chloride of boiling point 107°/12 mbar, $n_D^{20}$: 1.5368, are obtained. The following are obtained analogously:

5-chloro-2,3,4-trifluorobenzyl chloride, boiling point 78°/13 mbar; $n_D^{20}$: 1.4972, and
3-chloro-2,4,5-trifluorobenzyl chloride, boiling point 80°/16 mbar; $n_D^{20}$: 1.4966.

EXAMPLE 32

Chlorination of 5-chloro-2,3-trifluorobenzyl chloride 187 g (0.87 mol) of 5-chloro-2,3,4-trifluorobenzyl chloride are initially introduced and are chlorinated with less than the stoichiometric amount of chlorine, at 100°–105° C. with UV irradiation. According to assay by gas chromatography, the crude mixture contains 66% 5-chloro-2,3,4-trifluorobenzal chloride and 32% 5-chloro-2,3,4-trifluorobenzotrichloride. The following are obtained after fractional distillation:

94 g (43% of theory) of 5-chloro-2,3,4-trifluorobenzal chloride, boiling point 88°/12 mbar, $n_D^{20}$ 1.5082;

33 g (13% of theory) of 5-chloro-2,3,4-trifluorobenzotrichloride, boiling point 104°/12 mbar, $n_D^{20}$: 1.5235.

The following are obtained analogously:
3,5-dichloro-2,4-difluorobenzal chloride, boiling point 114°/14 mbar, $n_D^{20}$: 1.5443,
3,5-dichloro-2,4-difluorobenzotrichloride, boiling point 128°/14 mbar, melting point 43°.

EXAMPLE 33

5-Chloro-2,3,4-trifluorobenzaldehyde 72 g (0.29 mol) of 5-chloro-2,3,4-trifluorobenzal chloride are added to 220 g of 95% strength sulphuric acid at 40°, and stirring is continued at 40° until evolution of gas has finished.

The residue is poured onto ice, extracted with methylene chloride, and the organic phase is dried with sodium sulphate, concentrated and distilled. 18 g (32% of theory) of 5-chloro-2,3,4-trifluorobenzaldehyde of boiling point 73°/15 mbar, $n_D^{20}$: 1.5020 are obtained.

The following is obtained analogously:
3,5-dichloro-2,4-difluorobenzaldehyde, boiling point 98°14 mbar, melting point 32°.

It is understood that the specification and examples are illustrative but not limitative of the present invention and that other embodiments within the spirit and scope of the invention will suggest themselves to those skilled in the art.

| Example of a tablet containing end products tainable by using the compounds of the invention | |
|---|---|
| Each tablet contains: | |
| Compound of Example 1 | 583.0 mg |
| Hicrocrystalline cellulose | 55.0 mg |
| Maize starch | 72.0 mg |
| Poly(1-vinyl-2-pyrrolidone) insoluble | 30.0 mg |
| Highly disperse silica | 5.0 mg |
| Magnesium stearate | 5.0 mg |
| | 750.0 mg |
| The lacquer coating contains: | |
| Poly(O-hydroxypropyl O-methyl)cellulose 15 cp | 6.0 mg |
| Macrogol 4000 rec. INN (Polyethylene glycol DAB) | 2.0 mg |
| Titanium (IV) oxide | 2.0 mg |
| | 10.0 mg |

The end products have very low toxicity and exhibit a broad antibacterial spectrum towards Gram-positive and Gram-negative organisms, especially towards enterobacteriaceae; especially including those which are resistant to various antibiotics, such as, for example, penicillins, cephalosporins, aminoglycosides, sulphonamides and tetracyclines.

These valuable properties make it possible to use them as chemotherapeutic active compounds in medicine and as substances to preserve inorganic and organic materials, especially organic materials of all types, for example polymers, lubricants, dyes, fibres, leather, paper and wood, and foodstuffs and water.

The end products are active against a very broad spectrum of microorganisms. Using them, it is possible to control Gram-negative and Gram-positive bacteria and bacteroid microorganisms and to prevent, ameliorate and/or heal illnesses caused by these pathogens.

The end products are particularly active against bacteria and bacteroid microorganisms. Thus, they are especially suitable for the prophylaxis and chemotherapy of local and systemic infections caused by these pathogens in human and veterinary medicine.

For example, local and/or systemic illnesses which are caused by the following pathogens or by mixtures of the following pathogens can be treated and/or prevented: micrococcaceae, such as Staphylococci, for example *Staphylococcus aureus,* Staph. Epidermidis, (Staph.=Staphylococcus); Lactobacteriaceae, such as Streptococci, for example Streptococcus pyogenes, α- an β-haemolytic Streptococci, non-γ-haemolytic Streptococci, Enterococci and *Diplococcus pneumoniae* (Pneumococci) (Str.=Streptococcus); Enterobacteriacea, such as Escherichiae bacteria of the Escherichia group, for example *Escherichia coli,* Enterobacter bacteria, for example *E. aerogenes* and *E. cloacae* (E.=Enterobacter), Klebsiella bacteria, for example *K. pneumoniae* (K.=Klebsiella), Serratia, for example *Serratia marcescens,* Proteae bacteria of the Proteus group: Proteus, for example *Pr. vulgaris, Pr. morganii, Pr. rettgeri* and *Pr. mirabilis* (Pr.=Proteus); Pseudomonadaceae, such as Pseudomonas bacteria, for example *Ps. aeruginosa* (Ps.=Pseudomonas); Bacteroidaceae, such as Bacteroides bacteria, for example *Bacteroides fragilis* Mycoplasma, for example *Mycoplasma pneumoniae,* also Mycobacteria, for example *Mycobacterium tuberculosis, Mycobacterium leprae* and atypical Mycobacteria.

The above list of pathogens is purely illustrative and is in no way to be interpreted as restrictive. The following may be mentioned as examples of illnesses which can be prevented, ameliorate and/or healed by the end products: otitis, pharyngitis; pheumonia; peritonitis; pyelonephritis; cystitis; endocarditis, systemic infections; bronchitis; arthritis; local infections and septic illnesses.

The end products can be used as pharmaceutical preparations which in addition to non-toxic, inert pharmaceutically vehicles contain one or more compounds or which consist of one or more active compounds.

The end products can be used as pharmaceutical preparations in dosage units. This means that the preparation are in the form of individual parts, for example tablets, coated tablets, capsules, pills, suppositories and ampoules, of which the content of active compound corresponds to a fraction or a multiple of an individual dose. The dosage units can contain, for example, 1, 2, 3, or 4 individual doses or ½, ⅓ or ¼ of an individual dose. An individual dose preferably contains the amount of active compound which is given in one administration and which usually corresponds to a whole, a half, or a third or a quarter of a daily dose.

By non-toxic, inert pharmaceutically suitable vehicles there are to be understood solid, semi-solid or liquid diluents, fillers and formulation auxiliaries of all kinds.

Tablets, coated tablets, capsules, pills, granules, suppositories, solutions, suspensions and emulsions, pastes, ointments, gels, creams, lotions, powders and sprays may be mentioned as preferred pharmaceutical preparations.

Tablets, coated tablets, capsules, pills and granules can contain the active compound or compounds alongside the customary vehicles such as (a) fillers and extends, for example starches, lactose, sucrose, glucose, mannitol and silica, (b) binders, for example carboxymethylcellulose, alginates, gelatin and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol or glycerol monostearate, (h) adsorbents, for example kaolin and bentonite and (i) lubricants, for example talc, calcium and magnesium stearate and solid polyethylene glycols, or mixtures of these substances listed under (a) to (i).

The tablets, coated tablets, capsules, pills and granules can be provided with the customary coatings and shells, optionally containing opacifying agents, and can also be of such composition that they release the active compound or compound only, or preferentially, in a certain part of the intestinal tract, optionally in a delayed manner, examples of embedding compositions which can be used being polymeric substances and waxes.

The active end products, optionally together with one or more of the abovementioned vehicles, can also be in a microencapsulated form.

Suppositories can contain, in addition to the active end products, the customary water-soluble or water-insoluble vehicles, for example polyethylene glycols, fats, for example cacao fat, and higher esters (for example $C_{14}$-alcohol with $C_{16}$-fatty acids), or mixtures of these substances.

Ointments, pastes, creams and gels can contain the customary vehicles in addition to the active end products, for example animal and vegetable fats, waxes, paraffins, starch, tragacanth, cellulose derivatives, polyethylene glycols, silicones, bentonites, silica, talc and zinc oxide or mixtures of these substances.

Powders and sprays can contain the customary vehicles in addition to the active end products, for example lactose, talc, silica, aluminium hydroxide, calcium silicate and polyamide powders or mixtures of these substances. Sprays can additionally contain the customary propellants, for example chlorofluorohydrocarbons.

Solutions and emulsions can contain the customary vehicles in addition to the active compound or compounds, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, especially cottonseed oil, groundnut oil, maize germ oil, olive oil, castor oil and sesame oil, glycerol, glycerolformat, tetrahydrofurfuryl alcohol, polyethylene glycols and fatty acid esters of sorbitan, or mixtures of these substances.

For parenteral administration, the solutions and emulsions can also be in a sterile form which is isotonic with blood.

Suspensions can contain the customary vehicles in addition to the active compound or compounds, such as liquid diluents, for example water, ethyl alcohol or propylene glycol, suspending agents, for example ethoxylated isostearyl alcohols, polyoxyethylene sorbitol esters and soribtan esters, microcrystalline cellulose, aluminium metahydroxide, bentonite, agar-agar and tragacanth, or mixtures of these substances.

The formulation forms mentioned can also contain colourants, preservatives and additives which improve the odour and flavour, for example peppermint oil and eucalyptus oil, and sweeteners, for example saccharin.

The therapeutically active end products should preferably be present in the abovementioned pharmaceutical preparations in a concentration of about 0.1 to 99.5, preferably of about 0.5 to 95, % by weight of the total mixture.

The abovementioned pharmaceutically preparations can also contain other pharmaceutically active compounds in addition to the compounds according to the invention.

The abovementioned pharmaceutically preparations are manufactured in the usual manner according to known methods, for example by mixing the active compound or compounds with the vehicle or vehicles.

The active end products preparations can be administered locally, orally, parenterally, intraperitoneally and/or rectally, preferably orally or parenterally, such as intravenously or intramuscularly.

In general, it has proved advantageous both in human medicine and in veterinary medicine to administer the active compound or compounds in amounts of about 0.5 to about 500, preferably 5 to 100, mg/kg of body weight every 24 hours, optionally in the form of several individual administrations, in order to achieve the desired results. An individual administration contains the active compound or compounds preferably in amounts of about 1 to about 250, especially of 3 to 60, mg/kg of body weight. However, it can be necessary to deviate from the dosages mentioned and in particular to do so as a function of the nature and body weight of the subject to be treated, the nature and the severity of the illness, the nature of the preparation and of the administration of the medicine, and the time or interval over which the administration takes place.

Thus, it can suffice in some cases to manage with less than the abovementioned amount of active end product, whilst in other cases the abovementioned amount of active end product must be exceeded. The particular required optimum dosage and the type of administration of the active compounds can easily be decided by anyone skilled in the art, on the basis of this expert knowledge.

The end products can be administered in the customary concentrations and preparations together with the feed or with the feed preparations or with the drinking water. By this means, it is possible to prevent, ameliorate and/or heal an infection by Gram-negative or Gram-positive bacteria and by this means to achieve a promotion of growth and an improvement in the utilisation of the feed.

The MIC values of some of the end products are indicated in the table below.

As a comparison, corresponding MIC values for 1-ethyl-6-fluoro-1,4-dihydro-4-oxo-7-(1-piperazinyl)-3-quinolinecarboxylic acid ("norfloxacin"), which is disclosed in J. Med. Chem. 23, 1358 (1980), have been indicated, it emerging that the end products are superior to the known compounds.

| strain | MIC (mcg/ml) Example No. | | | | | | | | |
|---|---|---|---|---|---|---|---|---|---|
| | 1 | 2 | 3 | 5 | 6 | 7 | 8 | 10 | 17 |
| *E. coli* Neumann | ≦0.015 | ≦0.015 | ≦0.015 | ≦0.015 | ≦0.015 | ≦0.015 | ./. | ≦0.015 | ./. |
| T 7 | ≦0.015 | ≦0.015 | ≦0.015 | ≦0.015 | ≦0.015 | ≦0.015 | ≦0.015 | 0.025 | ./. |
| 445/7 | 4 | 8 | 8 | 8 | 4 | 16 | ./. | 16 | ./. |
| Klebsiella 63 | ≦0.015 | 0.03 | 0.03 | 0.03 | 0.015 | 0.06 | ./. | 0.125 | ./. |
| 6179 | 0.03 | 0.03 | ≦0.015 | 0.03 | 0.015 | 0.06 | ./. | 0.06 | ./. |
| Proteus 1017 | ≦0.015 | ./. | ./. | ./. | 0.06 | 0.125 | ./. | ./. | ./. |
| Providencia 12012 | ≦0.015 | 0.03 | ./. | ./. | 0.03 | ./. | ./. | ./. | ./. |
| 12052 | 8 | 16 | 16 | 32 | 4 | 16 | ./. | ./. | ./. |
| Staph. FK 422 | 0.25 | 0.25 | 0.25 | 0.25 | 0.025 | 0.5 | 0.06 | ./. | ≦0.015 |
| 1756 | 0.25 | 0.5 | 0.25 | 0.5 | 0.5 | 0.5 | 0.06 | ./. | ≦0.015 |
| 133 | 0.25 | 0.25 | 0.25 | 0.5 | 0.25 | 0.25 | 0.06 | ./. | ./. |
| Pseudom. Ellsworth | 0.06 | ./. | ./. | ./. | ./. | ./. | ./. | ./. | ./. |

| strain | MIC (mcg/ml) Example No. | | | | | | | | Norfloxacin |
|---|---|---|---|---|---|---|---|---|---|
| | 12 | 13 | 14 | 17 | 19 | 20 | 21 | 22 | |
| *E. coli* Neumann | ≦0.015 | ≦0.015 | ≦0.015 | ./. | ≦0.015 | ≦0.015 | ≦0.015 | ≦0.015 | 0.06 |
| T 7 | ≦0.015 | ≦0.015 | ≦0.015 | ./. | ≦0.015 | ≦0.015 | ≦0.015 | ≦0.015 | 0.03 |
| 445/7 | 8 | 8 | 2 | ./. | 1 | 1 | 1 | 2 | 16 |
| Klebsiella 63 | ≦0.015 | ≦0.015 | 0.06 | ./. | 0.03 | ≦0.015 | 0.06 | 0.03 | 0.125 |
| 6179 | 0.06 | 0.06 | 0.25 | ./. | 0.03 | 0.03 | 0.03 | 0.06 | 0.25 |
| Proteus 1017 | 0.03 | ≦0.015 | 0.125 | ./. | 0.03 | ≦0.015 | 0.03 | 0.06 | 0.03 |
| Providencia 12012 | ≦0.015 | ≦0.015 | 0.06 | ./. | 0.03 | 0.03 | 0.06 | 0.06 | 0.03 |
| 12052 | 16 | 16 | 16 | ./. | 4 | 4 | 1 | 2 | 64 |
| Staph. FK 422 | 0.25 | 0.25 | ./. | ≦0.015 | 0.06 | 0.06 | 0.125 | 0.125 | 0.5 |
| 1756 | 0.25 | 0.25 | ./. | ≦0.015 | 0.06 | 0.06 | 0.125 | 0.125 | 1 |
| 133 | 0.25 | 0.25 | ./. | ./. | 0.06 | 0.06 | 0.06 | 0.125 | 0.5 |
| Pseudom. Ellsworth | 0.125 | 0.125 | ./. | ./. | 0.125 | 0.25 | ./. | ./. | 0.125 |

We claim:

1. A process for the preparation of 2,4,5-trifluorobenzoyl fluoride, comprising reacting 2,4-dichloro-5-fluorobenzoyl chloride with potassium fluoride or with hydrofluoric acid prior to the reaction with potassium fluoride in a solvent at elevated temperature.

2. A process for the preparation of 2,3,4,5-tetrahalogenobenzene derivative of the formula

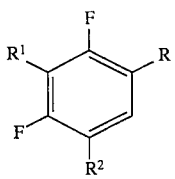

in which

R is —COCl or —COF, $R^1$ is Cl or F, and $R^2$ is Cl or F comprising reacting 2,3,4,5-tetrachlorobenzoyl chloride or 2,3,4,5-tetrachlorobenzoyl fluoride with potassium fluoride in a solvent at elevated temperature to yield a compound of said formula wherein R is —COF and thereafter optionally reacting said compound wherein R is —COF with $SiCl_4$ to yield a compound of said formula wherein R is —COCl.

3. The process according to claim 2, wherein the reaction with $SiCl_4$ is carried out in the presence of $AlCl_3$.

* * * * *